(12) United States Patent
Shekhar et al.

(10) Patent No.: US 6,748,267 B2
(45) Date of Patent: Jun. 8, 2004

(54) HEART THERAPY DEVICE

(75) Inventors: Mrigank Shekhar, Vancouver, WA (US); Tran Thong, Portland, OR (US); Indra B. Nigam, Tigard, OR (US)

(73) Assignee: Biotronik Mess-und Therapiegeraete GmbH & Co., Berlin (DE)

( * ) Notice: Subject to any disclaimer, the term of this patent is extended or adjusted under 35 U.S.C. 154(b) by 159 days.

(21) Appl. No.: 09/912,056

(22) Filed: Jul. 25, 2001

(65) Prior Publication Data

US 2003/0023272 A1 Jan. 30, 2003

(51) Int. Cl.$^7$ ................................................ A61N 1/36
(52) U.S. Cl. ................................ 607/4; 607/9; 607/14
(58) Field of Search ............................ 607/4, 5, 9, 14

(56) References Cited

U.S. PATENT DOCUMENTS

| | | |
|---|---|---|
| 4,181,133 A | 1/1980 | Kolenik et al. |
| 4,300,567 A | 11/1981 | Kolenik et al. |
| 5,002,052 A | 3/1991 | Haluska |
| 5,205,283 A | 4/1993 | Olson |
| 5,354,316 A | 10/1994 | Keimel |
| 5,379,776 A | 1/1995 | Murphy et al. |
| 5,447,519 A | 9/1995 | Peterson |
| 5,873,897 A * | 2/1999 | Armstrong et al. ........... 607/14 |

FOREIGN PATENT DOCUMENTS

| | | |
|---|---|---|
| DE | 44 39 256 A1 | 5/1995 |
| DE | 196 09 362 C1 | 6/1997 |
| DE | 691 24 719 T2 | 7/1997 |
| DE | 693 24 265 T2 | 12/1999 |

* cited by examiner

*Primary Examiner*—Angela D. Sykes
*Assistant Examiner*—Roderick Bradford
(74) *Attorney, Agent, or Firm*—Venable LLP; Robert Kinberg; Daniel G. Vivarelli, Jr.

(57) ABSTRACT

A heart therapy device includes a heart rate detector unit for detecting a heart rate, an evaluation and control unit adaptable to evaluate a measured heart rate and output a therapy control signal, and a therapy unit coupled to the output of the evaluation and control means for realizing at least one therapy having a predetermined therapy. The evaluation and control unit includes a three-area memory for storing heart rate value ranges, a heart rate discriminator for allocating a measured heart rate and outputting a first, second or third discriminator output signal, a stability evaluation unit for outputting a stability output signal and evaluating heart rate stability over a predetermined period of time in response to the output of the second heart rate discriminator output signal, and a logical processing unit for processing the second discriminator output.

11 Claims, 2 Drawing Sheets

HEART THERAPY DEVICE

BACKGROUND OF THE INVENTION

1. Field of the Invention

The invention relates to a heart therapy device. More specifically, the invention relates to an automatically implantable cardioverter/defibrillator (AICD) or a combined demand pacemaker/AICD.

2. Related Art

Automatic heart therapy devices are generally known and of daily medical use—particularly and for a longer period of time as implantable heart pacemakers for the treatment of bradycardiac and/or tachycardiac arrythmiae, but also increasingly as automatic defibrillators or cardioverters, combined pacemakers/defibrillators or as implantable drug dosing pumps, and the like.

Generic devices are also particularly known, which are equipped with one or more sensor(s) for sensing the cardiac rhythm in the patient's body, associated signal processing and editing means, and an evaluation and control unit. The latter calculates in each case an actual parameter or set of parameters in accordance with an algorithm stored in the device, depending on the value or the values of the heart rate from the amount of programmed operational parameters or therapy values. Therapy devices of said kind are known, which are configured for an automatic actuation or—a pre-programmed—switch-over from one operational mode into another depending upon the cardiac rhythm sensed in the patient's body. Such devices include the known demand heart pacemakers or automatic defibrillators, and the combination devices developed in recent times.

As early as the development and clinical application of so-called demand pacemakers, it has been known to specifically control heart pacemakers such that spontaneous cardiac actions are sensed, and the value of the heart rate or of the time intervals between determined heart actions (e.g. the RR intervals between successive ventricle actions) are assessed and compared with a predetermined nominal value, and that the pacemaker outputs stimulation pulses exactly at the moment, when the measured value is not within the range defined by the nominal value.

More modem devices of this type are microprocessor-controlled and offer the possibility of an individual, tailor-made programming for specific clinical symptoms from a plurality of pre-installed operational modes, by means of which and of associated operational parameters (in the following also called therapy values, as far as these are therapeutically relevant), a predetermined therapy is realized.

Within this framework, essential further developments of the concept of the demand pacemaker to the universal demand heart rhythm correction device have taken place, some of them starting from an increasingly refined subdivision of ranges of the heart rate continuum or RR interval continuum and which, depending upon which of the plurality of predetermined ranges the actual measured value lies, one of a plurality of defined therapies in each case definitely allocated to one range, is realized. By means of such a device, classical demand pacemaker operation in the case of bradycardia can be realized as well as conventional therapies of various tachycardiae (cf. for example U.S. Pat. No. 4,181,133) or, if necessary, even a defibrillation shock therapy (cf. U.S. Pat. No. 4,300,567).

Because the sole allocation of the heart rate to a predetermined range does not always reliably allow for a determination of the adequate therapy, additional classification criteria have been increasingly tested in the developments of the past years, and have been taken into account with the control algorithms; Such an example can be found in U.S. Pat. No. 5,379,776 (including the therein quoted sources).

Devices of the aforementioned kind are programmed on the occasion of implantation according to the clinical symptoms and, in some cases, to the living conditions (e.g. the average physical activities) of the patient, whereby the algorithm to be applied is also fixed for determining the therapy or the therapy value(s) in dependence of t he value(s) sensed in the body. At the time of regular aftercare examinations taking place at determined intervals, the set of operational modes and parameters, as well as—in case the therapy device disposes of several stored algorithms—the control algorithm to be applied can be modified by reprogramming.

U.S. Pat. No. 5,354,316 discloses a method and an apparatus for detecting and treating tachycardiae and fibrillations of a heart by means of specifically selected therapies of a combined pacemaker-cardioverter-defibrillator (PCD) apparatus of the generic kind. U.S. Pat. No 5,354,316, uses mutually overlapping range limits between tachycardia and fibrillation heart rate ranges. The assessment of the actually detected heart rhythm—in case of elevated heart rates—in the area of the ventricular tachycardia or of the ventricular fibrillation, ensues in the overlapping ranges by means of additional assessment criteria. It is specifically examined how many of the preceding intervals between successive ventricle actions fall into the overlapping range.

U.S. Pat. No. 5,447,519 discloses a similar method, whereby as a differentiation criterion between a ventricular tachycardia and ventricular fibrillation, the variability of the heart signal morphology (ECG curve profile) is referred to.

Another generic device is described in the Applicant's DE 196 09 362 C1. This heart therapy device likewise defines an overlapping region between two adjacent value ranges of a value measured in a patient's body. For controlling a selected, predetermined therapy, this device generally takes an evaluation of the history of the measurable variable (specifically the range allocation of the respective preceding value) or even of the therapy control value itself as the basis, in case the value is within the overlapping range.

OBJECTS OF THE INVENTION

It is an object of the invention to provide an improved therapy device of the generic kind, having a relatively simple and cost-efficient structure and yet being able to provide for an utmost careful but simultaneously efficient therapy of tachycardiac arrythmiae bordering on fibrillations—in particular in case of an atrial tachycardia.

SUMMARY OF THE INVENTION

The above and other objects of the invention can be solved by a heart therapy device. The heart therapy device includes a heart rate detection means for detecting a heart rate, an evaluation and control means coupled to the output of the heart rate detection means, the evaluation and control means having an output and being adaptable to evaluate a measured heart rate, including allocating the measured heart rate to one of a first, second and third heart rate value ranges, and output a therapy control signal in accordance with said allocation. The evaluation and control means includes a three-area memory for storing the first, second, and third heart rate value ranges, the heart rate value ranges ascending incrementally in value; a heart rate discriminator coupled to the heart rate detection means and the three-area memory for allocating a measured heart rate to the first, second or third heart rate value range, and for outputting a corresponding first, second or third discriminator output signal; a stability evaluation means for outputting a stability output signal and evaluating heart rate stability over a predetermined period of time in response to the output of the second heart rate discriminator output signal; and a logical processing unit for processing the second discriminator output signal and the stability output signal and for generating a second or third therapy control signal, while the first and third discriminator output signal are directly outputted as first and third therapy control signal, respectively. The heart therapy device also includes a therapy means coupled to the output of said evaluation and control means for realizing at least one therapy having a predetermined therapy parameter in response to the therapy control signal, in accordance with the measured heart rate lying within one of the predetermined value ranges, the therapy means being adaptable to output at least two different, uniquely pre-defined therapies in response to said second and third therapy control signal.

The invention embraces the essential idea of effecting an evaluation of high heart rates for deriving an adequate therapy by classifying the corresponding (high frequency) heart rate ranges into three adjacent ranges with fixed range limits. The invention thereby turns away from previous solutions according to the above-mentioned printed publications, in which the overlappings were in particular defined without rigidly predetermined limits. Moreover, the invention embraces the idea of using in the mid-range of the three value ranges apart from the heart rate itself, the result of a statistical evaluation of same—and namely specifically its stability in a preceding predetermined period of time—for deriving an appropriate therapy. By means of this approach, a simplification of the hardware and software configuration of the heart therapy device and an increase of the predictability and reliability of the therapy is achieved.

According to the an exemplary embodiment of the invention, it is provided that upon detection of a heart rate within the first value range (tachycardia zone 1), a first, uniquely pre-defined therapy control signal, and upon detection of a heart rate within the third value range (fibrillation zone), a third, likewise uniquely pre-defined therapy control signal is outputted. If, however, a heart rate is detected within the second value range (tachycardia zone 2), one of two different therapy control signals is outputted depending upon the stability of the heart rate. The stability criterion serves for distinguishing between "rapid" tachycardia ("flutter") and fibrillations of a—still—relatively low frequency. In particular, it is provided to output a second, specific therapy control signal in case of high stability for initiating a correction measure suitable for rapid tachycardia, whereas in the case of low stability, the third therapy control signal is outputted just as with a heart rate lying within the third value range.

This third therapy control signal, as a rule, will cause a shock therapy to be initiated, hence will trigger a cardioverter stage or defibrillator stage of the heart therapy device. As compared thereto, under certain circumstances, stimulation is not yet actually initiated at all by the first therapy control signal, rather, if necessary, the therapy device is first set into an operational state. However, the output of pacemaker pulse sequences to the heart may already be controlled by the first therapy signal—for example for an early control of the so-called re-entry tachycardia. By means of the second therapy control signal, a therapy is controlled, which lies in between the therapies with respect to its "aggressiveness", and which is used in tachycardia zone 1, for one, and in the fibrillation zone, for another. On the one hand, pacemaker pulse sequences can thereby be still concerned, e.g. the high frequency burst or ramp sequences (known per se), but also, on the other hand, a shock therapy (cardioversion) with one or more shock pulse(s) of relatively low energy. (The concept of low-energy cardioversion is also known per se and therefore does not require any further explanation here.)

The function of the therapy device outlined above hence resides in the finding that—with particular respect to atrial rhythm—there is a rate range of high-frequency tachycardia between the range of not life-endangering ("physiological") tachycardia and the range of life-endangering fibrillations, in which the stability criterion is referred to for distinguishing between tachycardia and fibrillations and for correspondingly differentiating the therapy. A stable atrial rhythm is treated as atrial flutter by a pacemaker stage of the therapy device, thereby allowing avoidance of cardioversion shocks, which are unnecessary for this stage and painful to the patient. Comparable heart rates with low stability, however, are a sign of menacing atrial fibrillation, and require activation of a cardiaversion or defibrillator stage.

It can already be seen from the statements made above that in an exemplary embodiment of the device, the heart rate detection means for detecting the atrial rate is connected with the patient's atrium—and namely in the practically most significant realization as an implantable device, as a rule via a detection electrode placed within the atrium and via a thereto connected measurement signal line. For special cases, other realizations are likewise possible, e.g. as an extracorporal device in clinical application and having extra-atrially arranged detection means. The use of the proposed device is further possible in high-frequency atrium arrythmiae—ventricular tachycardia/ventricular fibrillations.

One component of the proposed heart therapy device for realizing said therapy concept, is a three-area memory for storing the first, second and third value range of reference heart rates covering the total frequency range from relatively low-frequency, physiological tachycardia up to extremely high-frequency fibrillations. The limits between these ranges are fixedly determined for the ongoing operation—if necessary, however, adjustable by programming—and namely according to the specific indication adapted to the specific conditions of the respective patient. Said three-area memory co-operates with a multistage heart rate discriminator, which effects the allocation of a measured heart rate to one of the value ranges, and delivers an output signal characterizing the allocation result. Said output signal in particular is at the same time the first or third therapy control signal, respectively, as far as the actually detected heart rate lies within the first or third value range.

Moreover, a stability evaluation means for evaluating heart rate stability over a predetermined period of time (or a predetermined number of preceding heart actions) co-operates with said heart rate discriminator. Said stability evaluation means is activated insofar as a corresponding output signal of the heart rate discriminator indicates a value measured in the second value range. The stability evaluation means delivers an output signal characterizing the stability of the heart rate, which output signal is processed in a logical processing unit together with the discriminator output signal, so as to obtain the heart rate value as well as the therapy control signal reflecting the stability thereof. Hence, by means of the stability evaluation unit and the logical processing unit, a so to speak "therapy commutator"

between a less aggressive and a more aggressive heart rhythm correction measure between atrium (or ventricle) flutter, for one, and atrium (or ventricle) fibrillation, for another, is realized.

The stability evaluation means comprises the functional components necessary for the statistical evaluation of the heart rate values detected within a determined period of time, and namely in particular a heart rate measured value memory, a thereto connected statistical processing unit for determining a stability value, and a thereto connected stability discriminator stage, in which the actual stability value obtained with the statistical evaluation is compared with the predetermined (programmed) threshold value.

The therapy means of the device comprises at least one defibrillator, however, in the preferred embodiment, it further comprises a pacemaker means, and in particular also a therapy memory, by which, in response to the therapy control signals, in each case a predetermined therapy by the defibrillator or, optionally, the pacemaker, is activated. The therapy memory is connected to the output of the evaluation and control means in such a manner that the therapy control signals address in each case a predetermined memory area, where therapy data of a specific therapy is stored. Addressing of the first and third memory area ensues directly from the heart rate discriminator stage, whereas for addressing the second memory area the output signal of the stability evaluation means is necessarily used, and it is used in addition for addressing the third memory area. Hence, corresponding AND gates are provided here.

With respect to the specific therapies and hence also the therapy data stored in the therapy memory, there exist wide variation possibilities within the framework of the present invention, depending on the specific use of the device for a therapy of atrium or ventricle arrhythmiae, and on the configuration simply as a cardioverter/defibrillator or as a combined demand pacemaker/defibrillator. Thus, with a simple defibrillator, the first therapy control signal may cause the initiation of the operational state, whereas the second and third therapy control signal trigger shock therapies with different pulse energies. With a combined pacemaker/defibrillator, however, the first and second therapy control signals will preferably trigger a first and second stimulation pulse sequence, whereas the third therapy control signal triggers a shock pulse. For the remainder, reference is made to the basic explanations made above.

A reliable function of the proposed device requires permanent or periodical sampling of the heart rate, whereby at least with detection of a heart rate lying within the total value range of increased heart rates, the mentioned value range discrimination and, if necessary, stability evaluation, are triggered. For this purpose, a suitable controller is present in the evaluation and control means.

BRIEF DESCRIPTION OF THE DRAWINGS

Advantages and utilities of the invention result inter alia from the subclaims and the subsequent description of a preferred exemplary embodiment by means of the Figures. Therein show:

DETAILED DESCRIPTION OF THE INVENTION

Figure 1:
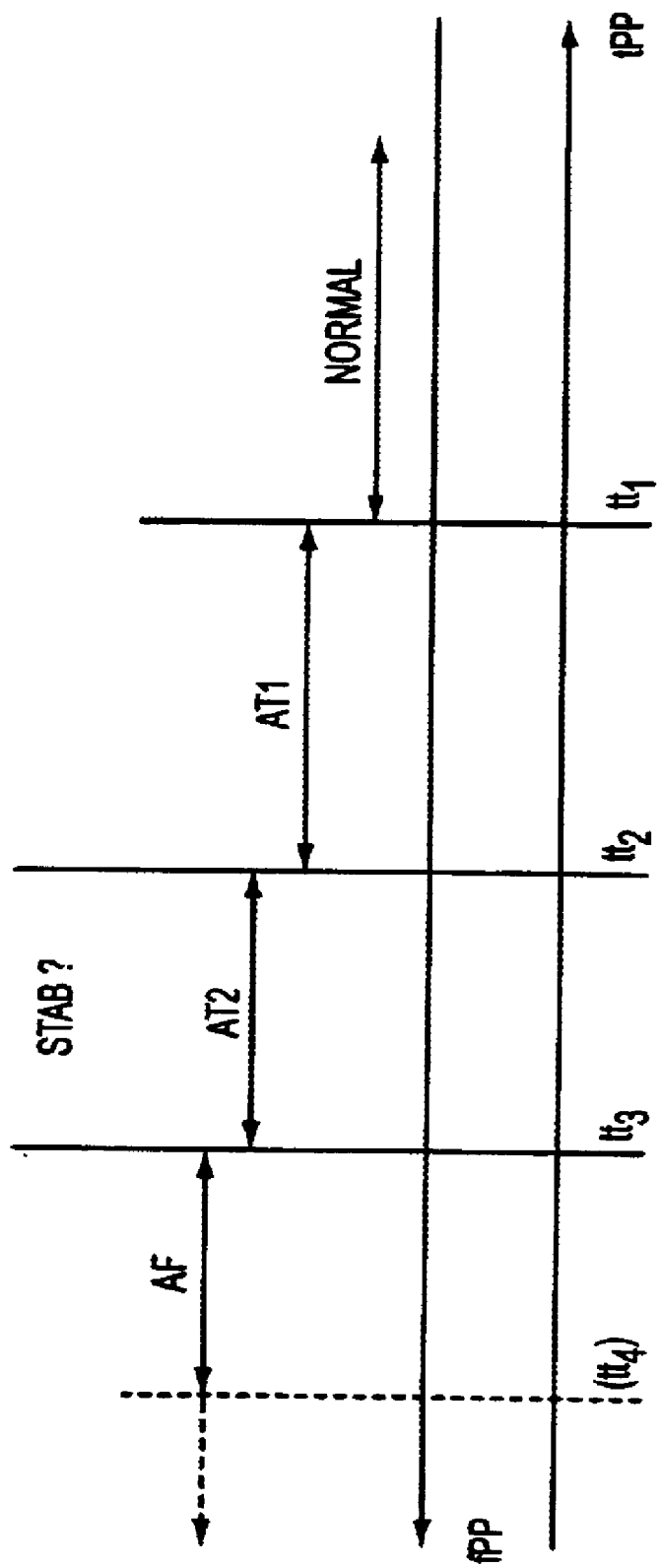
FIG. 1 a schematic representation of the continuous spectrum of ventricle intervals or ventricle rates classified in various value ranges for illustrating the function mode of the proposed heart therapy device.

FIG. 1 shows schematically in which way according to a practically important realization of the invention, the time or frequency continuum, tPP or fPP, respectively, of atrium actions is classified into adjacent value ranges for initiating appropriate therapies. (With values increasing towards the right side), the PP interval is outlined on the x-axis, and (with values increasing towards the left side), the atrial heart rate is outlined, respectively. The range of normal atrium rates is designated NORMAL, AT1 and AT2 designate two adjacent ranges of atrial tachycardia of different diagnostic and therapeutic importance, and AF designates the range of atrial fibrillation.

The limits $tt_1$ between the ranges NORMAL and AT1, $tt_2$ between the ranges AT1 and AT2, and $tt_3$ between the ranges AT2 and AF, are uniquely defined without overlappings according to the invention. For the range AF, an upper limit $tt_4$ may be fixed for process-technical reasons—which is symbolized in the Figure by means of a dashed line and the bracketing of $tt_4$—this third value range may, however, as well be open towards the upper side. As to evaluation and therapeutical measures in the individual ranges, reference is made to the above explanations.

Figure 2:
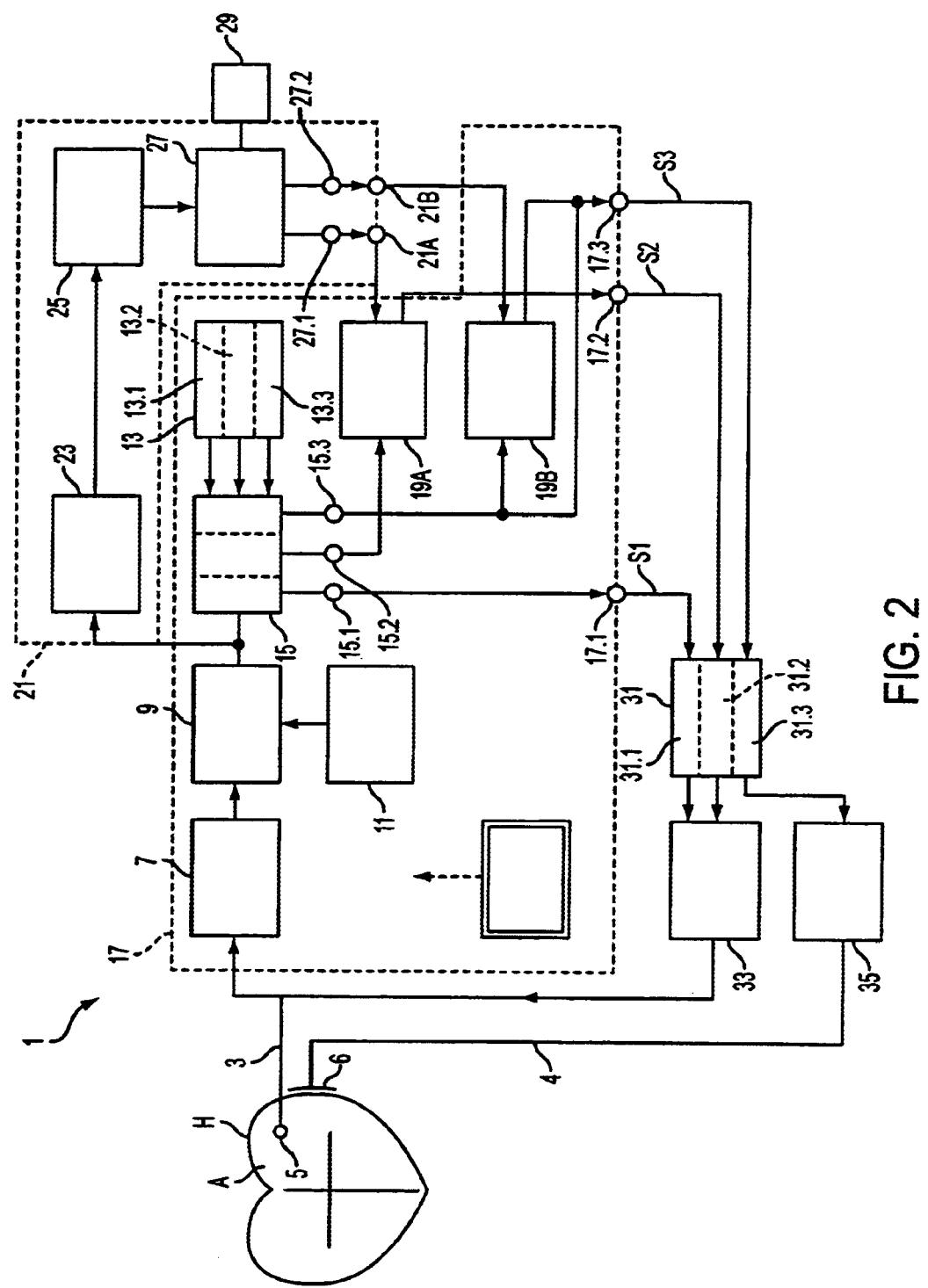
FIG. 2 a schematic representation of a heart therapy device according to an embodiment of the invention in the form of a functional block diagram.

In a schematic representation merely to be understood as a principle outline, FIG. 2 shows functional components of an implanted combined atrial pacemaker/defibrillator 1. At the input and output sides, said pacemaker/defibrillator 1 is connected via an electrode line 3 to a sensing and stimulation electrode 5 disposed in the atrium of a heart H, said electrode line 3 acting as a measuring signal line as well as a stimulation line. At the output side, it is in addition connected via a further electrode 4 to a defibrillation or shock electrode 6 at the heart H.

Electrode line 3 is connected to an input stage 7 comprising (in a configuration known per se) filter and amplifier stages for signal processing, and at the output of which, an interference-free and level-adjusted atrium signal is ready for being picked up. The output of the input stage 7 is connected to the input of a counter stage 9, the clock input of which is connected to a clock or timing pulse generator 11, and in which the fPP rate of the detected atrium actions (P peaks of the heart signal) is assessed.

An atrium rate reference value memory 13, having three memory areas 13.1, 13.2 and 13.3, is connected to a first input of an atrium rate discriminator stage 15, and the second input thereof is connected to the output of counter stage 9. The discriminator stage 15 is configured multistage—symbolized by dashed lines within block 15—and delivers an output signal characterizing the actually measured atrium rate as being part of one of the value ranges of the atrium rate (cf. FIG. 1) defined in the memory areas 13.1 through 13.3. This condition is illustrated by providing three different outputs 15.1, 15.2 and 15.3 of discriminator stage 15.

15.1 of discriminator stage 15 constitutes at the same time a first output 17.1 of the evaluation and control unit 17 of the atrium pacemaker/defibrillator 1, said first output 17.1 making a first therapy control signal S1 available. Output 15.3 of discriminator stage 15 is connected to a further output 17.3 of the evaluation and control means, which output 15.3 makes a third therapy control signal S3 available. Via a first logical AND gate 19A, output 15.2 of discriminator stage 15 is connected to a further output 17.2, which makes a second therapy control signal S2 available. Finally, a further logical AND gate 19B connects output 15.2 of the discriminator stage to the already mentioned output 17.3 of the evaluation and control means.

The AND gates 19A, 19B each are connected at their second input to an output 21A, 21B of a stability evaluation means 21. By this arrangement, the output of the mentioned third therapy control signal S3 is linked (besides the direct way) to a logical operation of the output signal of discriminator stage 15 and an output signal of the stability evaluation means 21, and a second therapy control signal S2 is necessarily linked at the second output 17.2 of discriminator stage 15 and stability evaluation means 21 as a result of a logical operation of the output signals. (As to the object and background of this logical operation, reference is made to the statements made further above.)

The stability evaluation means 21 comprises an atrium rate measured value memory 23 connected at its input side to the counter stage 9, and a statistical processing unit 25 connected to said memory 23 at its input side for computing a stability value of the atrium rate values stored in said measured value memory 23, which have been detected in a predetermined past period of time. To the output of processing unit 25, a first input of a stability discriminator stage 27 is connected, the other input of which is connected to a stability threshold value memory 29, and which, by means of a pre-programmed threshold value, carries out a threshold value discrimination of the stability value obtained as a result of the statistical processing in processing unit 25.

The result of the evaluation, depending upon whether the assessed stability value is above or below the threshold value—are two different output signals, which again is illustrated in the Figure by the representation of two outputs 27A, 27B of discriminator 27. Output 27A is connected to the second input of AND gate 19A, and output 27B is connected to the second input of AND gate 19B. In case the stability of the atrium rate is high, the AND gate 19A is acted upon with an output signal and the second therapy control signal S2 will thereby be generated, whereas in the case of lower stability of the atrium rate, the AND gate 19B is acted upon with an output signal of stability discriminator stage 27, and the third therapy control signal S3 will be generated.

To the outputs of evaluation and control means 17, a therapy memory 31 is connected having three memory areas 31.1, 31.2, 31.3, in which therapy data for different therapies for the correction of excessive atrium rates is stored. Specifically, memory area 31.1 is connected to output 17.1 at its input side, memory area 31.2 is connected to output 17.2, and memory area 31.3 is connected to output 17.3. The memory areas 31.1, 31.2 each contain a therapy data set for various pacemaker pulse sequences, and memory area 31.3 contains a therapy data set for a shock pulse therapy. Data from memory area 31.1 is fed to a pacemaker stage 33 of the combined atrium pacemaker/defibrillator 1, which, in answer thereto, outputs the respective and more specified pacemaker therapy via electrode line 3 and sensing and stimulation electrode 5 to atrium A. Therapy data from memory area 31.3 is fed to a defibrillator stage 35, which applies a shock pulse configured in accordance with said data via electrode line 4 and the specific shock electrode 6 to the atrium.

Controller unit 37 controls the above-mentioned rate detection and processing operations, the obtainment of the therapy control signals, and the output of the respective therapy to a patient's heart H.

The realization of the invention is not restricted to the above-described example but is likewise possible in a multitude of variations within the skilled person's activity.

What is claimed is:

1. A heart therapy device, comprising:
   a heart rate detection means for detecting a heart rate, the heart rate detection means having an output;
   an evaluation and control means coupled to the output of the heart rate detection means, the evaluation and control means having an output and being for evaluating a measured heart rate, including allocating the measured heart rate to one of a first, second and third heart rate value range, and for outputting a therapy control signal in accordance with said allocation, the evaluation and control means including:
      a three-area memory for storing the first, second, and third heart rate value ranges, the heart rate value ranges ascending incrementally in value,
      a heart rate discriminator coupled to the heart rate detection means and the three-area memory for allocating a measured heart rate to the first, second or third heart rate value range, and for outputting a corresponding first, second or third discriminator output signal,
      a stability evaluation means for evaluating heart rate stability over a predetermined period of time in response to the output of the second heart rate discriminator output signal and outputting a stability output signal, the stability evaluation means including:
         a heart rate measured value memory for storing a predetermined number of heart rate measured values or of all heart rate values measured within a predetermined period of time,
         a statistical processing unit connected to said heart rate measured value memory for statistically processing and assessing a heart rate stability value, and
         a stability discriminator stage for outputting a first stability signal if the heart rate stability is above a predetermined threshold value, and a second stability signal if the heart rate stability is below the predetermined threshold value,
      a logical processing unit for processing the second discriminator output signal and the stability output signal for generating a second or third therapy control signal, while the first and third discriminator output signals being directly outputted as first and third therapy control signals, respectively; and
   a therapy means coupled to the output of said evaluation and control means for producing at least two different, uniquely pre-defined therapies in response to said second and third therapy control signal, respectively,
   wherein the logical processing unit outputs the second therapy control signal in response to the generation of the first stability signal, and outputs the third therapy control signal in response to the generation of the second stability signal upon a heart rate lying within the second heart rate value range.

2. The heart therapy device according to claim 1, further comprising at least one sensing electrode and a measurement signal line coupled to the at least one sensing electrode, wherein the heart rate detection means is connectable to a patient's heart via the at least one sensing electrode and the measurement signal line.

3. An implantable defibrillator comprising:
   the heart therapy device according to claim 1.

4. A heart pacemaker comprising:
   the heart therapy device according to claim 1.

5. A combined pacemaker/defibrillator comprising:
the heart therapy device according to claim 1.

6. A heart therapy device, comprising:
a heart rate detection means for detecting a heart rate, the heart rate detection means having an output;
an evaluation and control means coupled to the output of the heart rate detection means, the evaluation and control means having an output and being for evaluating a measured heart rate, including allocating the measured heart rate to one of a first, second and third heart rate value range, and for outputting a therapy control signal in accordance with said allocation, the evaluation and control means including:
  a three-area memory for storing the first, second, and third heart rate value ranges, the heart rate value ranges ascending incrementally in value,
  a heart rate discriminator coupled to the heart rate detection means and the three-area memory for allocating a measured heart rate to the first, second or third heart rate value range, and for outputting a corresponding first, second or third discriminator output signal,
  a stability evaluation means for evaluating heart rate stability over a predetermined period of time in response to the output of the second heart rate discriminator output signal and outputting a stability output signal and, and
  a logical processing unit for processing the second discriminator output signal and the stability output signal for generating a second or third therapy control signal, while the first and third discriminator output signals being directly outputted as first and third therapy control signals, respectively; and
a therapy means coupled to the output of said evaluation and control means for producing at least two different, uniquely pre-defined therapies in response to said second and third therapy control signal, respectively, the therapy means including:
  a therapy memory having at least three freely addressable memory areas for storing the first, second, and third therapy control signals, respectively, the first and third memory area being directly addressable by the heart rate discriminator stage, the second memory area being exclusively addressable through a first logical AND gate, and the third memory area being additionally addressable through a second logical AND gate, wherein each of the logical AND gates have input sides that are connected to the outputs of the heart rate discriminator and the stability evaluation means.

7. The heart therapy device according to claim 6, wherein the second therapy control signal characterizes a heart rate of high stability occurring within the second heart rate value range, and the pacemaker means is for outputting a high-frequency burst pulse sequence or a high-frequency ramp pulse sequence in response to the second therapy control signal.

8. The heart therapy device according to claim 6, further comprising:
  a controller unit having a timing pulse generator and being controllable by the timing pulse generator, wherein the controller unit periodically polls the heart rate from the heart rate detection means and triggers a discrimination on the basis of the first, second, and third heart rate value ranges as a result of which an access control and address signal is outputted, the access control and address signal causing a therapy control parameter from the therapy means to be read out or to be denied.

9. An automatic heart pacemaker/defibrillator arrangement, comprising:
a heart rate detection means for detecting a heart rate, the heart rate detection means having an output;
an evaluation and control means coupled to the output of the heart rate detection means, the evaluation and control means having an output and being for evaluating a measured heart rate, including allocating the measured heart rate to one of a first, second and third heart rate value range, and for outputting a therapy control signal in accordance with said allocation, the evaluation and control means including:
  a three-area memory for storing the first, second, and third heart rate value ranges, the heart rate value ranges ascending incrementally in value,
  a heart rate discriminator coupled to the heart rate detection means and the three-area memory for allocating a measured heart rate to the first, second or third heart rate value range, and for outputting a corresponding first, second or third discriminator output signal,
  a stability evaluation means for evaluating heart rate stability over a predetermined period of time in response to the output of the second heart rate discriminator output signal and outputting a stability output signal and, and
  a logical processing unit for processing the second discriminator output signal and the stability output signal for generating a second or third therapy control signal,
while the first and third discriminator output signals being directly outputted as first and third therapy control signals, respectively;
a therapy means coupled to the output of said evaluation and control means for producing at least two different, uniquely pre-defined therapies in response to said second and third therapy control signal, respectively
a pacemaker means for delivering a predetermined stimulation pulse sequence in response to the second therapy control signal, or in response to the first therapy control signal; and
a defibrillator for delivering a shock pulse in response to the third therapy control signal.

10. The arrangement according to claim 9, wherein the first therapy control signal characterizes a heart rate occurring within the first heart rate value range, the second therapy control signal characterizes a heart rate of high stability occurring within the second heart rate value range, the pacemaker means is for outputting different stimulation pulse sequences as pacemaker therapies of stepped aggressiveness in response to the first and the second therapy control signals, whereby in response to the first therapy control signal a less aggressive pacemaker therapy is outputted than in response to the second therapy control signal.

11. An automatic heart pacemaker/defibrillator arrangement, comprising:
a heart rate detection means for detecting a heart rate, the heart rate detection means having an output;
an evaluation and control means coupled to the output of the heart rate detection means, the evaluation and control means having an output and being for evaluating a measured heart rate, including allocating the measured heart rate to one of a first, second and third heart rate value range, and for outputting a therapy control signal in accordance with said allocation, the evaluation and control means including:
- a three-area memory for storing the first, second, and third heart rate value ranges, the heart rate value ranges ascending incrementally in value,
- a heart rate discriminator coupled to the heart rate detection means and the three-area memory for allocating a measured heart rate to the first, second or third heart rate value range, and for outputting a corresponding first, second or third discriminator output signal,
- a stability evaluation means for evaluating heart rate stability over a predetermined period of time in response to the output of the second heart rate discriminator output signal and outputting a stability output signal, and
- a logical processing unit for processing the second discriminator output signal and the stability output signal for generating a second or third therapy control signal, while the first and third discriminator output signals being directly outputted as first and third therapy control signals, respectively; and
- a therapy means coupled to the output of said evaluation and control means for producing at least two different, uniquely pre-defined therapies in response to said second and third therapy control signal, respectively,
- wherein the second therapy control signal characterizes a heart rate of high stability occurring within the second heart rate value range, the third therapy control signal characterizes a heart rate of low stability occurring within the second heart rate value range, and the defibrillator is for outputting a shock pulse of low energy in response to the second therapy control signal, and a shock pulse of high energy in response to the third therapy control signal.

* * * * *